(12) United States Patent
Ruchti et al.

(10) Patent No.: US 7,620,674 B2
(45) Date of Patent: Nov. 17, 2009

(54) METHOD AND APPARATUS FOR ENHANCED ESTIMATION OF AN ANALYTE PROPERTY THROUGH MULTIPLE REGION TRANSFORMATION

(75) Inventors: Timothy L. Ruchti, Gilbert, AZ (US); Alexander D. Lorenz, Chandler, AZ (US); Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 767 days.

(21) Appl. No.: 10/976,530

(22) Filed: Oct. 29, 2004

(65) Prior Publication Data
US 2005/0149300 A1    Jul. 7, 2005

Related U.S. Application Data

(60) Provisional application No. 60/558,610, filed on Mar. 31, 2004.

(51) Int. Cl.
G06F 17/14 (2006.01)
G06F 7/38 (2006.01)

(52) U.S. Cl. .................. 708/400; 708/490
(58) Field of Classification Search .......... 708/400
See application file for complete search history.

(56) References Cited

U.S. PATENT DOCUMENTS

| | | | |
|---|---|---|---|
| 5,737,256 A * | 4/1998 | Nakagawa et al. | 708/400 |
| 6,115,673 A | 9/2000 | Malin | |
| 6,181,831 B1 * | 1/2001 | Sadjadian | 382/276 |
| 6,415,233 B1 * | 7/2002 | Haaland | 702/22 |
| 6,587,590 B1 * | 7/2003 | Pan | 382/250 |
| 6,871,169 B1 | 3/2005 | Hazen | |
| 2002/0107858 A1 | 8/2002 | Lundahl | |
| 2005/0177607 A1 * | 8/2005 | Dor et al. | 708/400 |

* cited by examiner

Primary Examiner—Tan V Mai
(74) Attorney, Agent, or Firm—Michael A. Glenn; Glenn Patent Group

(57) ABSTRACT

The invention comprises transformation of a section of a data block independently of the transformation of separate or overlapping data blocks to determine a property related to the original matrix, where each of the separate or overlapping data blocks are derived from an original data matrix. The transformation enhances parameters of a first data block over a given region of an axis of the data matrix, such as signal-to-noise, without affecting analysis of a second data block derived from the data matrix. This allows for enhancement of analysis of an analyte property, such as concentration, represented within the original data matrix. A separate decomposition and factor selection for each selected data matrix is performed with subsequent score matrix concatenation. The combined score matrix is used to generate a model that is subsequently used to estimate a property, such as concentration represented in the original data matrix.

18 Claims, 11 Drawing Sheets

METHOD AND APPARATUS FOR ENHANCED ESTIMATION OF AN ANALYTE PROPERTY THROUGH MULTIPLE REGION TRANSFORMATION

CROSS REFERENCE TO RELATED APPLICATIONS

This document claims priority to U.S. provisional patent application No. 60/558,610 filed Mar. 31, 2004. This document also claims priority to U.S. patent application Ser. No. 10/472,856, filed Sep. 18, 2003, which claims priority to PCT application No. PCT/US03/07065, filed Mar. 7, 2003, which claims priority to U.S. provisional patent application No. 60/362,885, filed Mar. 8, 2002 all of which are incorporated herein in their entirety by this reference thereto.

BACKGROUND OF THE INVENTION

1. Field of the Invention

The invention relates generally to an enhancement of estimation of an analyte property or concentration represented by a data matrix. In particular, the invention relates to a method and apparatus for enhanced estimation of an analyte property through multiple region transformation.

2. Discussion of the Prior Art

Preprocessing and multivariate analysis are well-established tools for extracting a spectroscopic signal, usually quite small, of a target analyte from a data matrix in the presence of noise, instrument variations, environmental effects, and interfering components. Various methods and devices are described that employ preprocessing and multivariate analysis to determine an analyte signal.

R. Barnes, J. Brasch, D. Purdy, W. Lougheed, Non-invasive determination of analyte concentration in body of mammals, U.S. Pat. No. 5,379,764, (Jan. 10, 1995) describe a method in which a subject is irradiated with near-infrared (NIR) radiation, resulting absorbance spectra are preprocessed, and the resulting spectra are analyzed using multivariate techniques to obtain a value for analyte concentration.

J. Ivaldi, D. Tracy, R. Hoult, R. Spragg, Method and apparatus for comparing spectra, U.S. Pat. No. 5,308,982, (May 3, 1994) describe a method and apparatus in which a matrix model is derived from the measured spectrum of an analyte and interferents. A spectrum is generated for an unknown sample. The spectrum is treated with first and second derivatives. Multiple linear least squares regression is then used to fit the model to the sample spectrum and compute a concentration for the analyte in the sample spectrum.

L. Nygaard, T. Lapp, B. Arnvidarson, Method of determining urea in milk, U.S. Pat. No. 5,252,829, (Oct. 12, 1993) describe a method and apparatus for measuring the concentration of urea in a milk sample using attenuated total reflectance spectroscopy. Preprocessing techniques are not taught or used. Calibration techniques, such as partial least squares, principal component regression, multiple linear regression, and artificial neural networks are used to determine spectral contributions of known components and relate them back to the urea concentration in milk.

M. Robinson, K. Ward, R. Eaton, D. Haaland, Method of and apparatus for determining the similarity of a biological analyte from a model constructed from known biological fluids, U.S. Pat. No. 4,975,581 (Dec. 4, 1990) describe an attenuated total reflectance method and apparatus for determining analyte concentration in a biological sample based on a comparison of infrared energy absorption between a set of samples with known analyte concentrations and a sample where the comparison is performed using a model.

Calibration development with techniques, such as multiple linear regression (MLR), principal component regression (PCR), partial least squares regression (PLS), and nonlinear calibration methods have some inherent disadvantages. One well-documented problem with multivariate analysis is that noise in the data creates error in the model. This is especially true when too many factors are employed in the development of the model. The modeling error results in subsequent prediction matrices with erroneously high error levels. See, for example, H. Martens, T. Naes, *Multivariate Calibration* John Wiley & Sons, p. 352 (1989); or K. Beebe, B. Kowalski, *An Introduction to Multivariate Calibration and Analysis, Anal. Chem.* 59, 1007A-1017A (1987). Complicating this issue is the fact that the initial factors of factor decomposition are dominated by a region of high variance to the detriment of analysis of a region with smaller variance.

For example, a few factors may model a region having:
A. a high degree of co-linearity;
B. a high signal to noise ratio;
C. minor or readily modeled instrument variations;
D. a relatively low contribution of environmental effects; or
E. a minimal number of readily modeled interfering signals.

Other regions require a higher number of factors in order to sufficiently model the analytical signal. This is the case when:
A. the data are not fully linear;
B. a low signal to noise region is analyzed;
C. instrument drift changes the spectral response over time; or
D. a large number of spectrally interfering components are present.

Finally, due to low signal to noise, a particular region may provide limited utility for model development.

In traditional chemometric analysis, a single preprocessing routine is applied over an entire axis of a data matrix. For example, an entire spectral region is selected for a single preprocessing routine. This means that a single preprocessing routine is selected despite the region to region variation spectral state, such as signal, noise, and resolution. Thus, for a given region within a spectrum, selection of the appropriate preprocessing routine to adequately enhance the signal-to-noise ratio results in all other spectral regions using the same preprocessing routine. In many cases, another spectral region is optimally enhanced with different preprocessing. That is, one preprocessing routine is not optimal for multiple regions of a spectrum where the underlying signal and noise structures are different in different spectral regions. This is based on the fact that the signal is non-uniform with respect to spectral region and the noise is typically heteroscedastic with wavelength. Thus, a compromise in the single preprocessing routine for different spectral regions becomes necessary and results in a sub-optimal extraction of the signal. There exists, therefore, a need in the art for a preprocessing system with separate routines for each region of an axis of a data matrix, such as a wavelength or spectral region, to enhance independently the combination of spectral regions analyzed, and to enhance fully the signal to noise ratio of each wavelength region or spectral region.

Similarly, in traditional calibration development using multivariate techniques, such as PCR or PLS, a single number of factors is applied over an axis of a data matrix. For example, an entire spectral region is selected for a single number of factors. This means that for a given region within the spectrum, selection of the appropriate number of spectral factors to model the signal adequately results in all other spectral regions using the same number of factors. In many cases, another spectral region is optimally modeled with a number of factors that is different than the optimal number of factors used for the first spectral region. Thus, a compromise between wavelength selection and the number of factors to incorporate into the model becomes necessary. There exists, therefore, a need in the art for a routine that allows the number of factors for each region of an axis, such as a wavelength or spectral region, to be chosen independently of the number of factors used to model a different wavelength or spectral region.

K. Hazen, S. Thennadil, T. Ruchti, Combinative multivariate calibration that enhances prediction ability through removal of over-modeled regions, PCT patent application no. PCT/US01/21703, (Jul. 9, 2001) describe a calibration where different spectral regions are analyzed with a differing number of factors. Selection of an appropriate number of factors for each spectral region allows removal of noisy regions before inclusion into the calibration model.

An enhancement of estimation of an analyte property is presented that allows for optimization of decomposition of a given spectral range independently of other separate or overlapping spectral ranges. An additional preprocessing step is optional, and is performed prior to decomposition, after decomposition, or is performed both prior to and after decomposition. A combination step concatenates the scores matrices of the individual decompositions to arrive at a composite scores matrix for subsequent calibration development. The developed calibration is subsequently applied to a new matrix, such as a spectrum, to perform an estimation of a target analyte concentration or property.

SUMMARY OF THE INVENTION

The invention provides for transformation of a given data matrix independently of the transformation of separate or overlapping data matrices i to determine a property related to the original matrix, where each of the separate or overlapping data matrices are derived from an original data matrix. The transformation enhances parameters, such as signal-to-noise, that allow for the enhancement of analysis of the analyte concentration or an analyte property represented within the original data matrix. In a first embodiment of the invention, a decomposition and factor selection for each selected data matrix is performed. In a second embodiment, each data matrix is independently preprocessed.

Data matrices representative of a sample contain information related to a signal, have noise that hinders analysis of the matrix, and often have interfering features related to constituents within the sample or the instrument. The signal, noise, and interference representative of the sample are often not evenly distributed throughout the data matrix. For example, the features representative of the analyte or constituent of interest can have different signal strengths and/or resolution and/or frequency content along an axis of the matrix, such as wavelength, time, or position. In another example, the noise characteristics can be heteroscedastic along an axis of the matrix. Similarly, interference characteristics, such as signal, noise, and resolution often vary along an axis of the data matrix that represents a sample. Because transformations are designed to enhance particular features and/or remove or minimize particular noise types, a single transformation of the data matrix to enhance matrix parameters, such as signal-to-noise, is sub-optimal. Separate transformations of different regions of the data matrix result in optimal extraction of underlying information because the transformations are optimized to the particular characteristics of the selected region of the data matrix. Similarly, the varying nature of the signal, noise, and interference within sub-matrices necessitate separate analysis to optimally extract analyte information.

Extraction techniques are presented herein for the noninvasive analysis of glucose concentration in tissue and/or blood using near-IR spectroscopy. It is noted that the invention presented, herein, is applicable to other fields, such as data matrices obtained in other spectroscopic techniques and to data matrices obtained using chromatographic techniques. Further, while examples herein are directed toward constituent concentration determination in biomedical methods, the invention applies to many additional fields, such as industrial, pharmaceutical, and agricultural methods and/or techniques. In its broadest sense, the invention is applicable to data matrices with at least one measurement associated with each frequency, time, distance, position, wavelength, or related x-axis determination, where the measurement signal, noise, and/or interference varies along the x-axis.

Finally, while the invention is described with respect to a single data axis, it is readily applicable to applications involving multi-dimensional measurements, such as imaging systems, time-resolved systems, target recognition, image recognition, and multi-dimensional signal processing, as well as to techniques such as fluorescence and speech processing.

DETAILED DESCRIPTION

A method and apparatus are disclosed that transform a given data matrix independently of the transformation of separate or overlapping data matrices, where each of the separate or overlapping data matrices are derived from an original data matrix. The transformation enhances parameters, such as signal to noise, that allow for enhancement of analysis of analyte concentration, such as glucose in tissue, or a composition represented within the original data matrix. In a first embodiment of the invention, the invention performs a decomposition and factor selection for each selected data matrix. In a second embodiment, each data matrix is independently preprocessed.

In the first embodiment of the invention, at least two matrices of data are selected from an original data matrix, optional preprocessing is performed, each matrix is decomposed, selected scores from each decomposition are concatenated to arrive at a composite score matrix, and a calibration is developed using the composite score matrix. The calibration model is used on subsequent data to estimate a target analyte concentration, composition, or identification from an estimation matrix (prediction matrix). The process is depicted schematically in FIG. 1.

Initial Data

Figure 1:
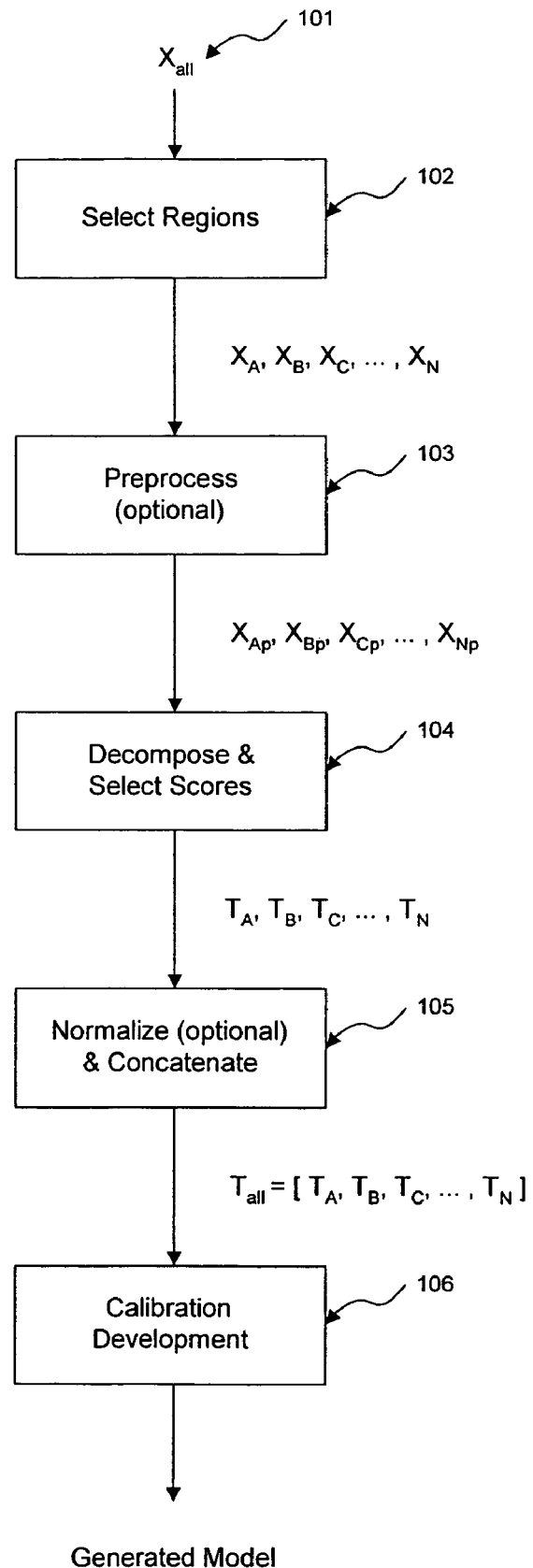
FIG. 1 is a schematic diagram of the steps of processing matrix regions independently of each other and combining the results into a calibration model according to the invention.

In construction of a calibration, a matrix of data $X_{all}$ 101 is used as in FIG. 1. An example data matrix is a matrix of spectral responses as a function of wavelength or time. Spectra are typically collected, in single beam mode, as intensities or voltages and are converted to absorbance measurements by electronic means or mathematical means, as is well understood in the art. Alternatively, spectra are collected directly as absorbance spectra with the use of a double beam spectrometer. For illustrative purposes, $X_{all}$ in FIG. 1 are an initial set of spectra in a format that is already converted to absorbance units. However, it is recognized that the invention functions on spectroscopic responses, such as single beam spectra in intensity units or on alternative transformations or representations of raw detected signals, such as interferograms. Alternatively, the invention functions on matrices of data generated using chromatography as described infra. Alternatively, the invention functions on spectroscopic images that involve a wavelength axis and a secondary axis, such as position (spatial), and time.

The following two sections discuss region selection 102, such as wavelength, position, or time selection and preprocessing 103. The optional preprocessing step can occur before region selection, after region selection, neither before nor after region selection, or both before and after region selection. Selection of the preprocessing order is often related to the particular data characteristics.

Spectral Region Selection

The invention uses two to n regions, where $n \geq 2$, regions, FIG. 1. For clarity, the subsequent discussion uses an example of a matrix $X_{all}$ of spectral responses as a function of wavelength. The matrices associates with the selected spectral regions are designated $X_A, X_B, X_C, \ldots, X_N$, where $X_A$ is a matrix associated with the first spectral region and $X_N$ is the matrix associated with the last spectral region. The spectral regions are all independent of each of the other spectral regions and each of the spectral regions are equal to or subsets of the original spectral region associated with $X_{all}$. Hence the selected spectra regions can abut, overlap, and/or be separated by an unselected spectral region. This is readily accomplished, for example, by copying the original matrix $X_{all}$ and generating each selected matrix from a copy.

Preprocessing

The invention allows preprocessing of selected matrices independently of each other. The signal, noise, and interferences of each region are not necessarily the same. The independent preprocessing of each spectral region allows for optimization of the signal-to-noise ratio or other figure of merit of each region. Preprocessing of the matrices designated $X_A$, $X_B, X_C, \ldots, X_N$ results in the matrices designated $X_{Ap}, X_{Bp}, X_{Cp}, \ldots, X_{Np}$, as depicted in FIG. 1.

There exist a large number of preprocessing techniques and methods, such as sample selection, outlier analysis, smoothing, $n^{th}$ derivative calculation (where n is an integer $\geq 0$), filtering, correction, multiplicative scatter correction, mean-centering, and normalization. Some of these techniques are, preferably, performed on an independent copy of the original matrix $X_{all}$ prior to narrowing to the selected wavelength range so that edge effects are not incorporated into the selected region. For example, this is true of filtering with convolutions, such as Savitsky-Golay smoothing or derivatization. However, filtering on the selected region is feasible, especially with narrower convolution functions or with broader selected regions. Other preprocessing techniques are linear operations, and are thus equivalent if performed before or after the spectral region selection. For example, mean centering of a selected spectral region before selection of the region is equivalent to mean centering the same spectral region after selection of the spectral region. Preprocessing techniques are, optionally, used together in sequence. For example, an n-point Savitsky-Golay convolution of a matrix associated with a selected spectral region is followed by another technique, such as mean centering. The actual parameters for a given preprocessing technique are frequently optimized iteratively with a monitoring data set and a response function.

Noise is often heteroscedastic, non-uniform along a matrix axis, and/or pink, such as noise with a varying frequency center with respect to spectral region. Non-uniform noise results from a number of sources, such as temperature, instrumentation, applied processing, and changes in the local environment with time. Removal of noise is best accomplished with processing techniques designed to remove the particular noise type. Therefore, processing separate parts of a data matrix independently with different noise reduction techniques is beneficial. This is especially true because some preprocessing techniques effect other regions of the matrix.

Decomposition and Factor Section

Generally, a matrix X is decomposed into a loading matrix and a score matrix according to $X=TV^T$. The invention decomposes each selected matrix, $X_A, X_B, X_C, \ldots, X_N$, or preprocessed matrix, $X_{Ap}, X_{Bp}, X_{Cp}, \ldots, X_{Np}$, independently, FIG. 1. For each decomposition, a score matrix is generated as is known in the art. A number of score vectors for each matrix are selected to represent the matrix 104. Score selection is well known in the art. Selection of too few scores inadequately models the signal and interference, while selection of too many scores incorporates noise. Often, the optimal number of scores is selected iteratively with a test or monitoring data set. The selected score matrices associated with the selected or preprocessed matrices are designated $T_A, T_B, T_C, \ldots, T_N$, in FIG. 1. The invention allows independently selecting a number of factors to represent each of said N score matrices, such that a number of factors representing a first of said N matrices is less than, equal to, or greater than a number of factors representing a second of said N matrices. Herein, this process is referred to as independently selecting a number of factors for each of said N score matrices.

As described, supra, the initial loading in a decomposition is dependent upon the variance of the matrix. If a large variance is present in the matrix, the large variance dominates the decomposition. Therefore, to obtain the highest signal-to-noise ratio in the initial factors of a region where variance is low in a data matrix that contains a region of high variance, the region of low variance is preferably separately decomposed. This separate decomposition yields higher signal-to-noise levels with fewer factors. Similarly, spectral information is extracted with fewer factors. Extraction of information with fewer factors has benefits, such as a more robust model.

When a data matrix is decomposed, the maximum variance of the matrix dominates the initial factors. This affects the ability of the decomposition to represent other regions of the matrix optimally with the initial factors. Removal of the region dominating the variance prior to decomposition allows extraction of information from different regions with fewer factors with a better noise signal-to-noise ratio. A separate decomposition that uses a separate number of factors is then employed for the region with greater variance. This allows separate decomposition of two, or more, regions and for extraction of information with fewer factors.

Concatenization

The invention concatenates the score matrices $T_A$, $T_B$, $T_C$, ..., $T_N$, according to equation 1 to yield $T_{all}$ 105.

$$T_{all} = [T_A, T_B, T_C, \ldots, T_N] \quad (1)$$

Optionally, the individual score matrices $T_A$, $T_B$, $T_C$, ..., $T_N$ are normalized prior to concatenating. A calibration is developed 106 using $T_{all}$.

Calibration and Measurement

The decomposition and model used to estimate a tissue analyte or property are performed and developed through the processes of factor decomposition and calibration, respectively, on the basis of an exemplary set of data and associated reference analytes or proprieties. Together, the set of data and the associated properties values constitute the calibration set. During measurement, the prior decomposition and model are applied to data blocks that have been processed as described in FIGS. 1 to 3.

The decomposition is typically performed using factor analysis methods, such as principle component analysis, evolving factor analysis, or partial least-squares regression. The decomposition, based on the calibration set, produces a matrix of loadings or eigenvectors that, when applied to a data block, produce a matrix of scores with each row corresponding to a sample and each column corresponding to a loading.

Alternately, the data blocks are decomposed through by a Fourier series, a wavelet based analysis, or a Taylor series expansion. These and other similar methods produce a matrix of weights, parameters, or coefficients that correspond to the scores described in the invention.

In each sub-block of data, only a subset of scores are selected for calibration to reduce the dimensionality of the data. The scores of the calibration set, after concatenation, are used together with reference target variables to determine the model, $f(\cdot)$. The method for designing the structure of $f(\cdot)$ is generally through the process of system of identification or, in the linear case, through the process of factor selection. The model parameters are calculated using known methods including multivariate regression or weighted multivariate regression [see, for example, N. Draper, H. Smith, *Applied Regression Analysis*, 2d.ed., John Wiley and Sons, New York (1981)], principal component regression [see, for example, H. Martens, T. Naes, *Multivariate Calibration*, John Wiley and Sons, New York (1989)], partial least squares regression [see, for example, P. Geladi, B. Kowalski, *Partial least-squares regression: a tutorial*, Analytica Chimica Acta, 185, pp.1-17, (1986)], or artificial neural networks [see, for example, S. Haykin, *Neural Networks: A Comprehensive Foundation*, Prentice Hall, Upper Saddle River N.J. (1994)].

In the preferred embodiment, multiple linear regression is used to calculate a set of regression coefficients, which represents the model, from the score and property value matrices.

EXAMPLE 1

A specific example of separately decomposing two matrices with one of the matrices having a region of larger variance is provided. As described below, the example uses near-infrared (near-IR) spectra collected noninvasively to build a model subsequently used to estimate glucose concentrations. The initial matrix of spectra, $X_{all}$, are processed with a traditional single decomposition analysis for comparison with the two separate decomposition approach.

In this example, decomposition of two spectral regions of a data matrix of noninvasive spectra of human tissue is performed so that determination of blood glucose concentration is provided. For comparative purposes, a parallel analysis with a single decomposition is also performed. A detailed description follows.

It is determined that signal, noise, resolution, and pathlength considerations often dictate that the analysis of noninvasive near-IR spectra of aqueous solutions having small analytical signals, such as the first overtone region band spectral region from 1450 to 1900 nm. It is determined that the first overtone region is preferably included in multivariate analyses to obtain adequate signal-to-noise levels of glucose. Inclusion of the first overtone region often requires many factors to fully model the less intense and more overlapped analytical signals, with the result of over-modeling of the second overtone region from 1100 to 1450 nm, if included in the same model. Such a limitation is dictated by traditional multivariate methods that require a single number of factors for the entire spectral region being analyzed. The inventive approach allows analysis of signal in a high variance region or in a region of low signal strength, such as the first overtone region, at the same time that sample information, such as pathlength, is extracted from a second region, such as the second overtone region. As the following discussion reveals, applying the inventive approach leads to smaller standard errors of estimates. The calibration data set is the same for both models. Three glucose analyzers, as described supra, were used to collect 1427 calibration spectra, after outlier determination, of eight individuals during a total of thirteen separate visits over a nine week period. A prediction data set is generated using a separate glucose analyzer. The prediction data set represents 249 samples collected from six individuals, i.e. four males and two females.

Figure 2:
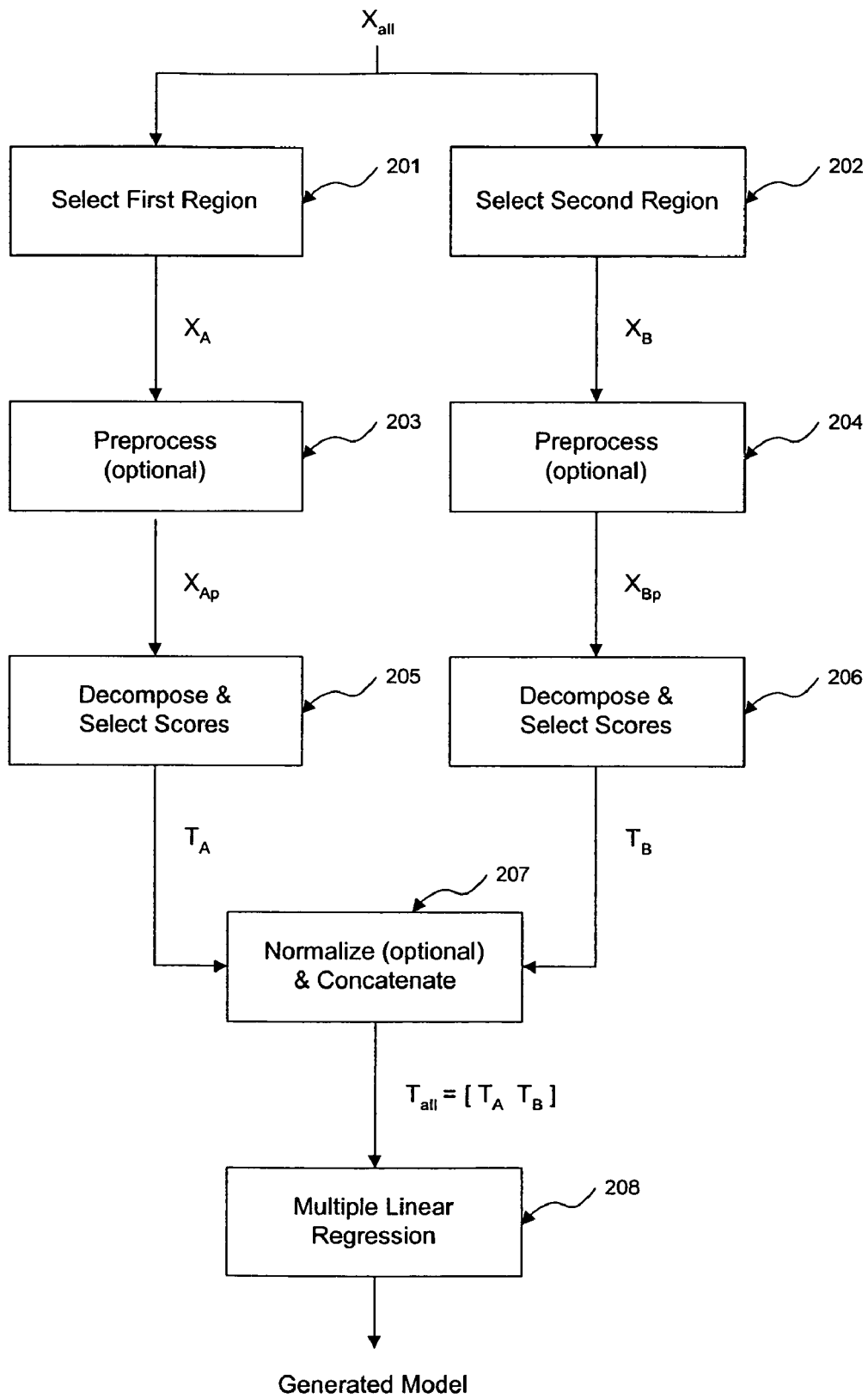
FIG. 2 is an example of independent decomposition of two regions according to the invention.

A flowchart for the separate decomposition of two matrices is provided in FIG. 2. In this example, the initial matrix $X_{all}$ is duplicated and two matrices of two spectral regions $X_A$ 201 and $X_B$ 202 are generated from $X_{all}$. In this example, $X_A$ and $X_B$ do not overlap. Each matrix $X_A$ and $X_B$ are separately preprocessed yielding $X_{Ap}$ 203 and $X_{Bp}$ 204. The preprocessed matrices are separately decomposed. A number of scores from each resulting score matrix are selected resulting in score matrices $T_A$ 205 and $T_B$ 206. The two truncated score matrices are normalized and concatenated to form $T_{all}$ 207, multiple linear regression 208 is performed on the resulting matrix, and a calibration model is generated. The model is subsequently used to estimate an analyte concentration from a new set of data.

Figure 3:
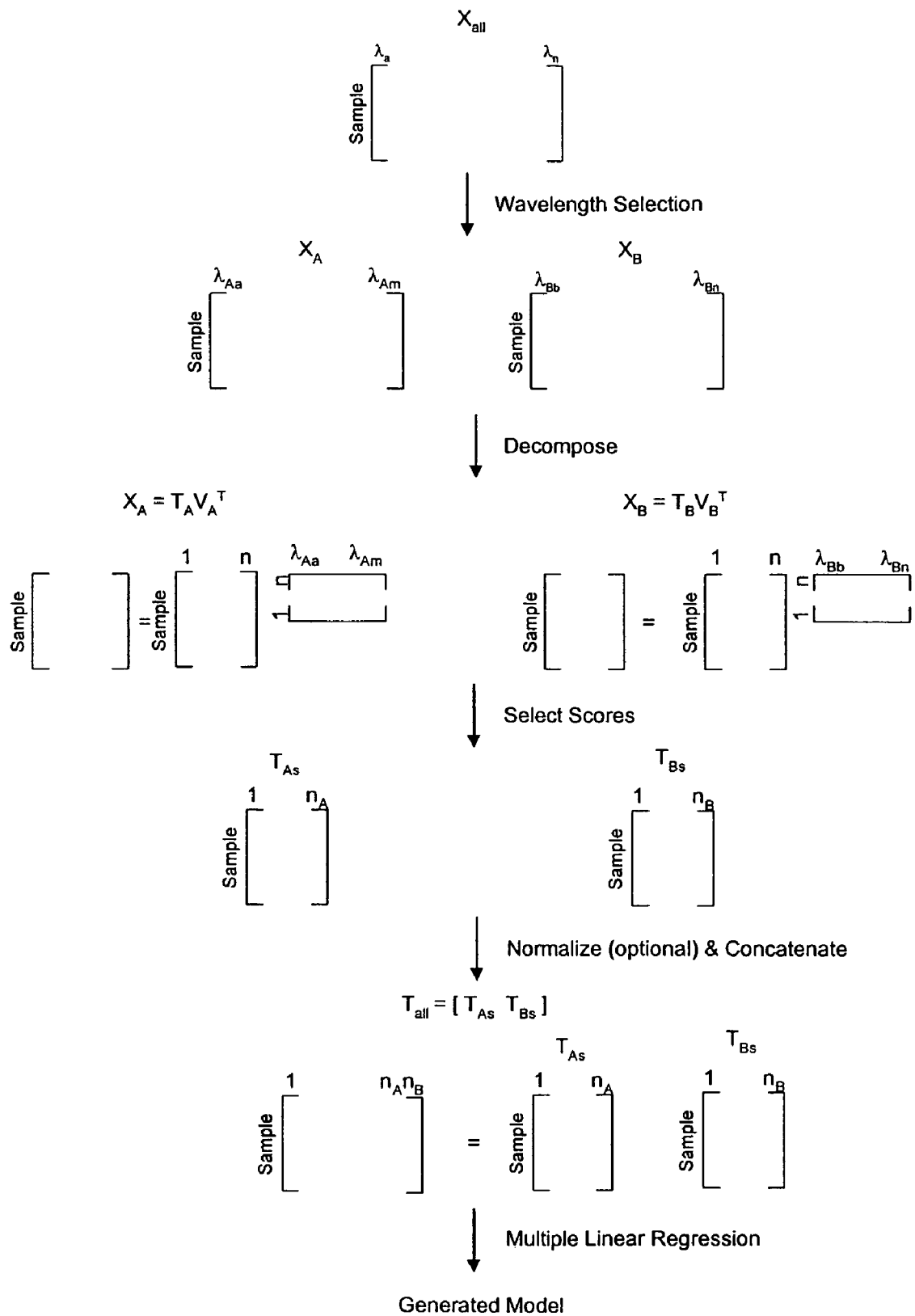
FIG. 3 provides a detailed example of independent decomposition and subsequent concatenization of two regions according to the invention.

A more detailed flowchart of a separate decomposition step of two matrices is provided in FIG. 3, in terms of spectra represented as absorbance, or alternatively intensity, as a function of wavelength. In this example, the initial matrix $X_{all}$ is duplicated and two matrices of two spectral regions $X_A$ and $X_B$ are generated from $X_{all}$. The matrices are separately decomposed into corresponding score T and loading V matrices. A number of scores from each resulting score matrix $T_s$ and $T_B$ are selected resulting in score matrices $T_{As}$ and $T_{Bs}$.

The two truncated score matrices are concatenated to form $T_{all}$, multiple linear regression, or other calibration development, is performed on the resulting matrix, and a calibration model is generated. The model is subsequently used to estimate an analyte concentration from a new set of data.

Instrumentation

A diffuse reflectance based glucose analyzer was used to collect calibration and estimation (prediction) near-infrared spectra. The glucose analyzer included a sample module and a base module coupled by a communication bundle. The sample module included a source, backreflector, and optics. The communication bundle carried power and optical signal. The base module included a grating and a linear array detector. Wavelength and intensity references were collected and used. In this case, the wavelength reference was polystyrene and the intensity reference was polystyrene. The sample was a human forearm. Calibration data were collected with a fixed probe, bottom-up measurement sampling the dorsal aspect of a forearm, where the probe had three bundlets. Prediction spectra were collected with a floating probe, top down fiber probe sampling the volar aspect of a forearm with a single collection fiber. Processor means are used as are well known in the art. While the example is to a particular analyzer, the invention is applicable to data matrices generated from a wide number of related analyzers and sample sites, such as those described in U.S. patent application Ser. No. 10/472,856 (attorney docket number SENS0011), which is incorporated herein in its entirety by this reference thereto.

Initial Spectra

Figure 4:
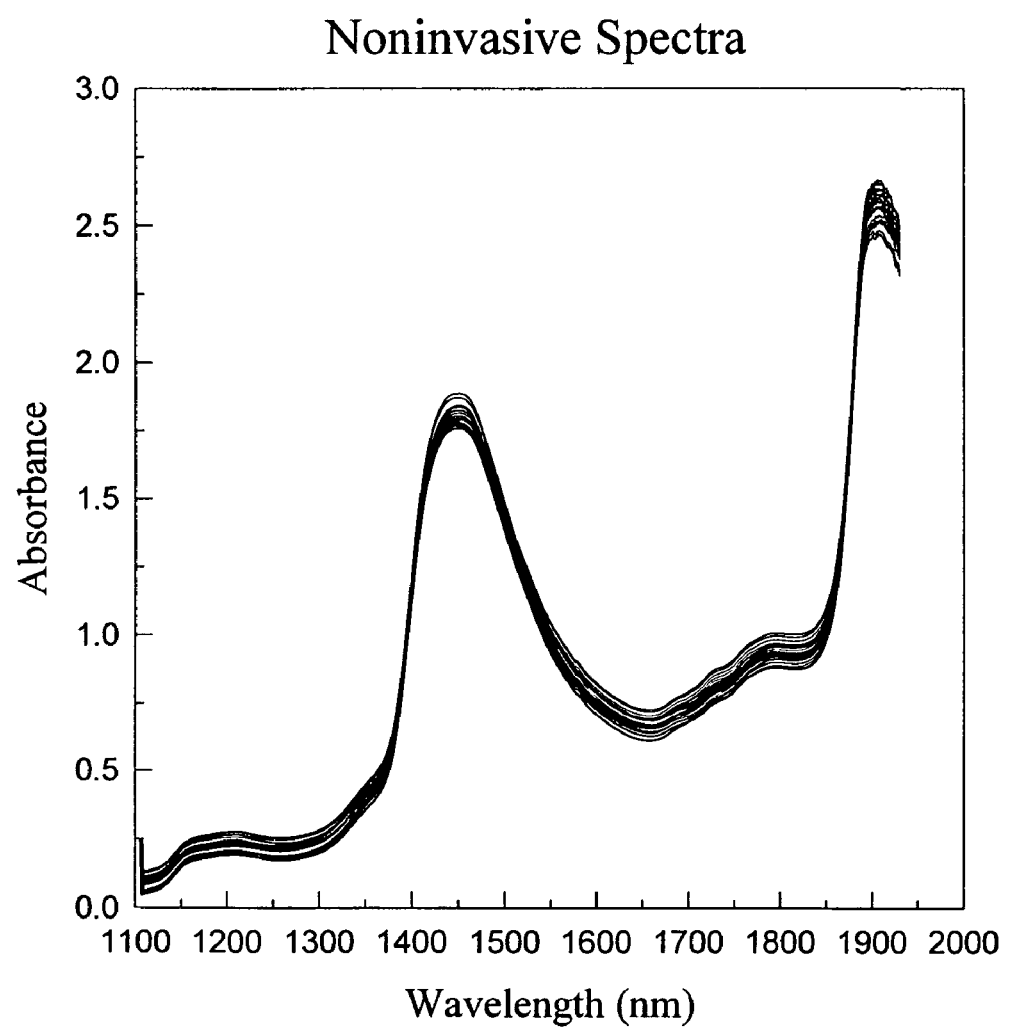
FIG. 4 shows spectra collected noninvasively.

The calibration data set is converted to absorbance units and is represented by $X_{all}$ in FIG. 2, which covers the range 1100 to 1930 nm. The noninvasive near-infrared absorbance spectra presented in FIG. 4 represent every fiftieth sample of $X_{all}$ in this example. Large water absorbance bands are present around 1450 nm and 1930 nm. The glucose information is present throughout the spectra, however, it is dominantly present in the first overtone region. The second overtone region contains scattering information.

Analysis

For comparative purposes, analysis of a single spectral range is performed in parallel with the inventive algorithm, which is used to decompose the spectra in two separate regions. Both analyses start with the same matrix of collected spectra, $X_{all}$.

In the near-infrared, several differences in spectral characteristics as a function of wavelength occur.

First, spectral features (signals) are broader and less intense with decreasing wavelength. For example, the combination band region, from 2000 to 2500 nm, has narrower and more intense absorbance band features related to the same fundamental chemical bond or interaction than the corresponding features in the first overtone region, 1450 to 2000 nm. The first overtone absorbance features are similarly narrower and more intense than the corresponding features in the second overtone region, 1100 to 1450 nm. Similar logic extends to both higher and lower energy regions of the electromagnetic spectrum. Other techniques, such as those based on chromatography, also have signal intensity and resolution that is dependent upon the measurement axis, such as time. Therefore, different spectral processing techniques are optimal for different regions of the spectrum. For example, a wider convolution function, such as a Savitsky-Golay smoothing or derivative function with a larger number of points, is often applied to the wider signal bands of the second overtone region while a narrower convolution function, such as a Savitsky-Golay smoothing or derivative function with a fewer number of points, is more applicable to signal extraction in the first overtone region.

Second, noise in the near-infrared is often wavelength dependent. In this case, the noise of detectors increases with wavelength, especially from 1500 to 1900 nm. Removal of noise is best accomplished with processing techniques designed to remove the particular noise type. In addition, the optimal method for filtering noise is dependent on the frequency content of the noise and the frequency content of the signal. The data region is filtered, such that the signal-to-noise ratio is enhanced. This is described in U.S. provisional patent application Ser. No. 60/558,610 filed Mar. 31, 2004 (attorney docket no. SENS0007PR), which is incorporated herein in its entirety by this reference thereto. Therefore, processing separate parts of a data matrix independently with different noise reduction techniques is beneficial.

Third, resolution is often wavelength dependent. In this example, the resolution of the analyzer is not constant from 1100 to 1930 nm due to the spectrometer design. In this example, the resolution is generally degraded in the middle of the spectral range due to the grating/detector coupling. Therefore, processing separate parts of the data matrix independently where the processing is resolution dependent is beneficial.

Figure 5:
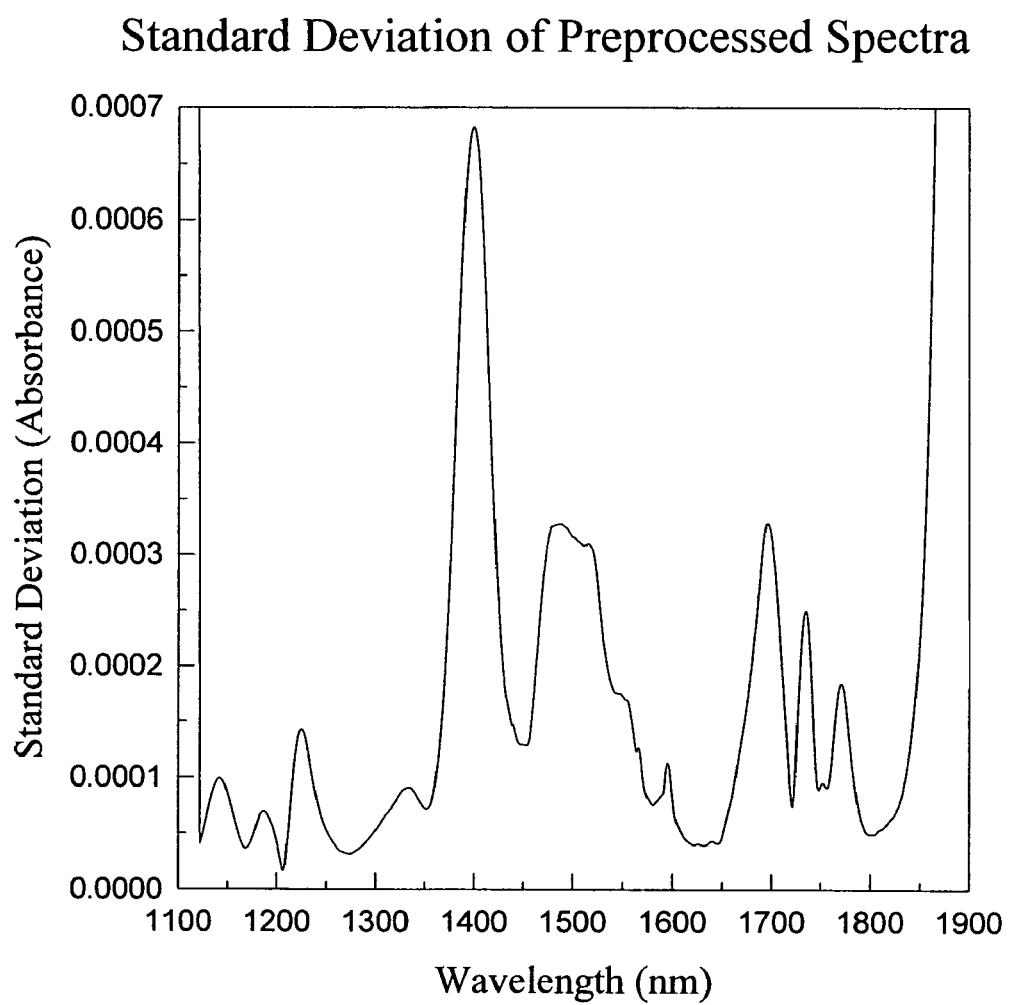
FIG. 5 shows the standard deviation of the noninvasive spectra.

The matrix $X_{all}$ represented in FIG. 4 has two dominant water absorbance bands at 1450 and 1930 nm. The standard deviation of the preprocessed spectra, described infra, is calculated and presented as a function of wavelength in FIG. 5. Several regions of high variation are observed. From 1100 to 1120 nm, the large absorbance of the longpass filter results in higher variance and a higher standard deviation. Similarly, the very large water absorbance band centered at 1930 nm results in a large standard deviation at wavelengths longer than 1850 nm. In this example, prior to decomposition both of these regions are removed in both the single and double decomposition approaches. The water absorbance band centered at 1450 nm results in variances that are larger than the variances in the remaining spectral region from approximately 1125 to 1850 nm. The dip in variance observed at 1440 nm results from the first derivative preprocessing. The variance in the 1350 to 1500 nm region is larger than that observed in the second overtone region. Therefore, the first decomposition factor of the entire region is dominated by this region about 1450 nm. Total exclusion of the higher variance region typically results in poorer standard error of estimates and thus the region about 1450 nm is preferably maintained in the analysis. However, the initial decomposition factors representing the information, such as scattering, observed in the second overtone region extract less information than if the higher variance region was removed. Therefore, an approach to optimizing the second overtone region information in the first few factors is to decompose this region separately. Decomposition of a larger spectral region containing the greater variance results in the extraction of additional data, such as absorbance features of the sample site. Extraction of small absorbance features, such as glucose, in the presence of larger absorbance features, such as water, fat, and protein requires more factors. The optimal number of factors to extract the key information in separate spectral regions is therefore different. The separate deconvolution of multiple regions allows this optimal extraction as is demonstrated below by example.

Figure 6:
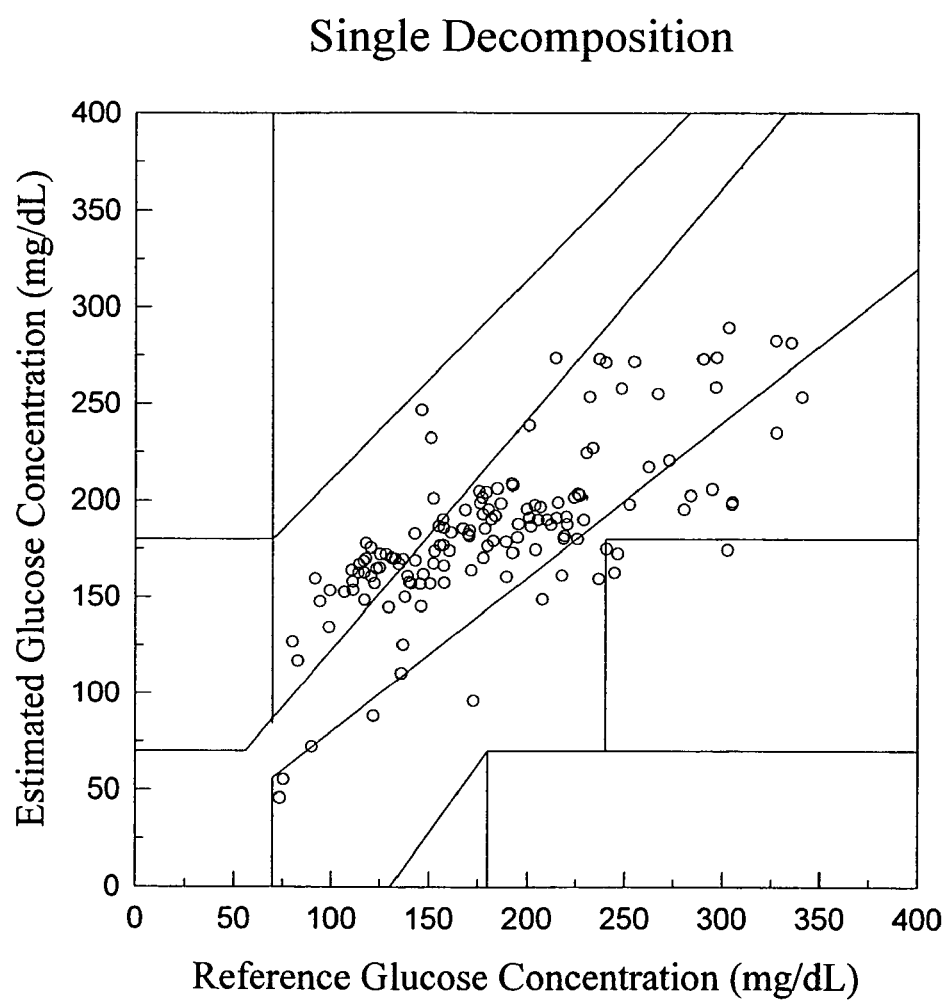
FIG. 6 shows noninvasive glucose concentration estimations in a concentration correlation plot.

The single decomposition approach applied to $X_{all}$ preprocesses the spectra in three steps: 1) a 27-point first derivative Savitsky-Golay smoothing convolution; 2) selection of a data matrix associated with the 1150 to 1850 nm spectral range;

and 3) mean centering. The resulting matrix is analyzed with principal component regression (PCR) using a total of 44 factors. A new matrix of 249 samples is generated. The resulting standard error of estimation, which is also loosely referred to as a standard error of prediction (SEP), on the new samples is 40.8 mg/dL. The resulting glucose concentration estimations are presented in FIG. 6, which is overlaid onto a Clarke error grid. A total of 66.4, 32.2, and 1.4% of the resulting glucose estimations fell into the A, B, and D regions of a Clarke error grid, respectively.

Figure 7:
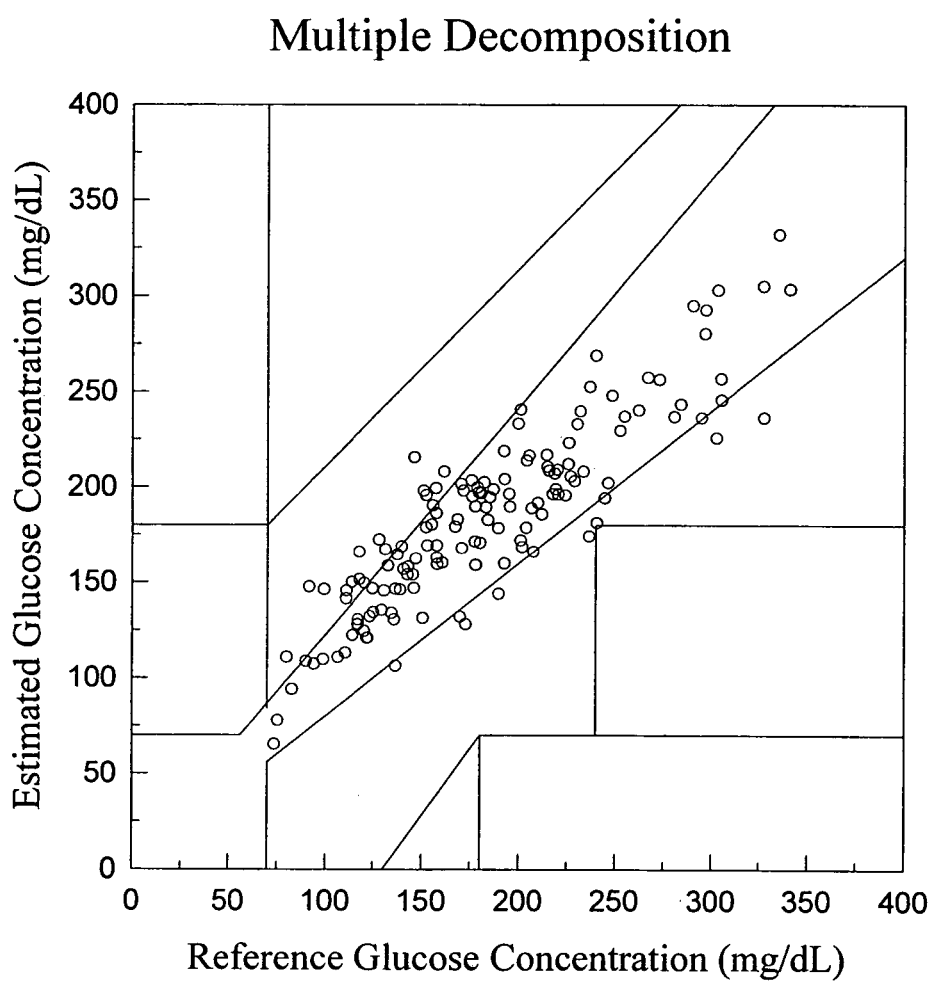
FIG. 7 provides noninvasive glucose concentration estimations in a concentration correlation plot according to the invention.

The dual region decomposition approach uses a first matrix associated with the spectral range of 1200 to 1375 nm and a second matrix associated with the spectral range of 1375 to 1850 nm. The first region is preprocessed in three steps: 1) a three-point first derivative Savitsky-Golay smoothing convolution; 2) selection of a data matrix associated with the 1200 to 1375 nm spectral range; and 3) mean centering. The resulting matrix is decomposed and twelve factors are selected. The second region is preprocessed in three steps: 1) a 27-point first derivative Savitsky-Golay smoothing convolution; 2) selection of a data matrix associated with the 1375 to 1850 nm spectral range; and 3) mean centering. The resulting matrix is decomposed and 45 factors are selected. The scores matrices are then normalized, combined, and multiple linear regression is used to form a model. Use of the model, on the same data as used in the traditional approach above, results in a standard error of estimation of 32.5 mg/dL. The resulting glucose concentration estimations are presented in FIG. 7, which is overlaid onto a Clarke error grid. The glucose concentration estimate result in 4.2, 25.6, and 0.2% of the estimations being in the A, B, and D regions of the Clarke error grid, respectively. Compared to the single decomposition approach, the dual decomposition approach results in a reduced standard error of estimation and an increased percentage of point in the 'A' region of a Clarke error grid thus providing a demonstration of the increased analytical performance of the dual decomposition approach compared to the single decomposition approach.

The separate decomposition of the individual matrices allows removal of the region of large variance from the first matrix associated with the 1200 to 1375 nm spectral range. This allows the initial factors in this region to capture major sources of variation represented by this region, such as scattering information and pathlength. Other ranges are, optionally, used to extract the scattering or pathlength information such as 1100 to 1400 nm, ranges in the second overtone spectral region, or subsets of ranges therein. The separate deconvolution of the 1375 to 1850 nm spectral range and the selection of more factors allows modeling of smaller variations, such as those due to fat, protein, and glucose. Combined, as demonstrated in this example, the separate decomposition of the individual matrices results in a reduction of the SEP from 40.8 to 32.5 mg/dL and resulted in an improved distribution of results in terms of the Clarke error grid analysis. Optionally, other ranges are used to extract glucose information such as 1100 to 2500 nm, and regions in any of the combination band, first overtone, or second overtone.

EXAMPLE 2

The analyzers used in the first example were used to collect the data set used in this example. The single data matrix based decomposition uses a calibration matrix representing 2939 spectra collected on a total of six subjects using three analyzers over a five week period. The two decomposition approach uses a data set representing 846 spectra collected using five subjects on a total of six analyzers. For both the single and multiple decomposition calibrations, a single prediction data set is used. The prediction matrix represents 141 samples from five different subjects collected over a total of six visits on a single analyzer over a period of eight days collected roughly five months after the end of collection of the calibration data matrices.

Figure 8:
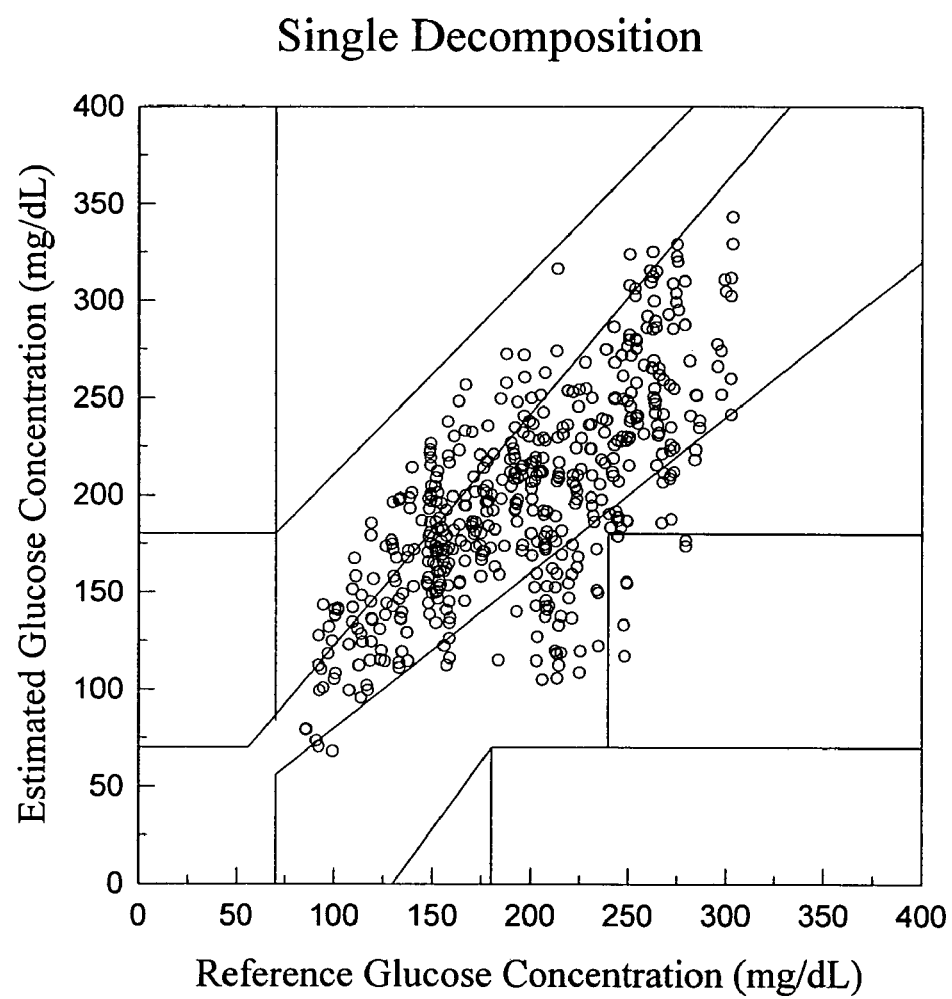
FIG. 8 shows a second example of noninvasive glucose concentration estimations in a concentration correlation plot.

The single decomposition approach applied to $X_{all}$ in absorbance preprocesses the spectra in four steps: 1) a 41-point first derivative Savitsky-Golay smoothing convolution; 2) multiplicative scatter correction; 3) mean centering; and 4) selection of a data matrix associated with the 1250 to 1850 nm spectral range. The resulting matrix is analyzed with principal component regression (PCR) with a total of 14 factors. A new matrix of 141 samples is generated. The resulting standard error of estimation, which is also loosely referred to as a standard error of prediction (SEP), on the new samples is 42.1 mg/dL. The resulting glucose concentration estimations are presented in FIG. 8, which is overlaid onto a Clarke error grid. A total of 60.3, 38.3, and 1.4% of the resulting glucose estimations fell into the A, B, and D regions of a Clarke error grid, respectively. The resulting F-value is 2.09.

Figure 9:
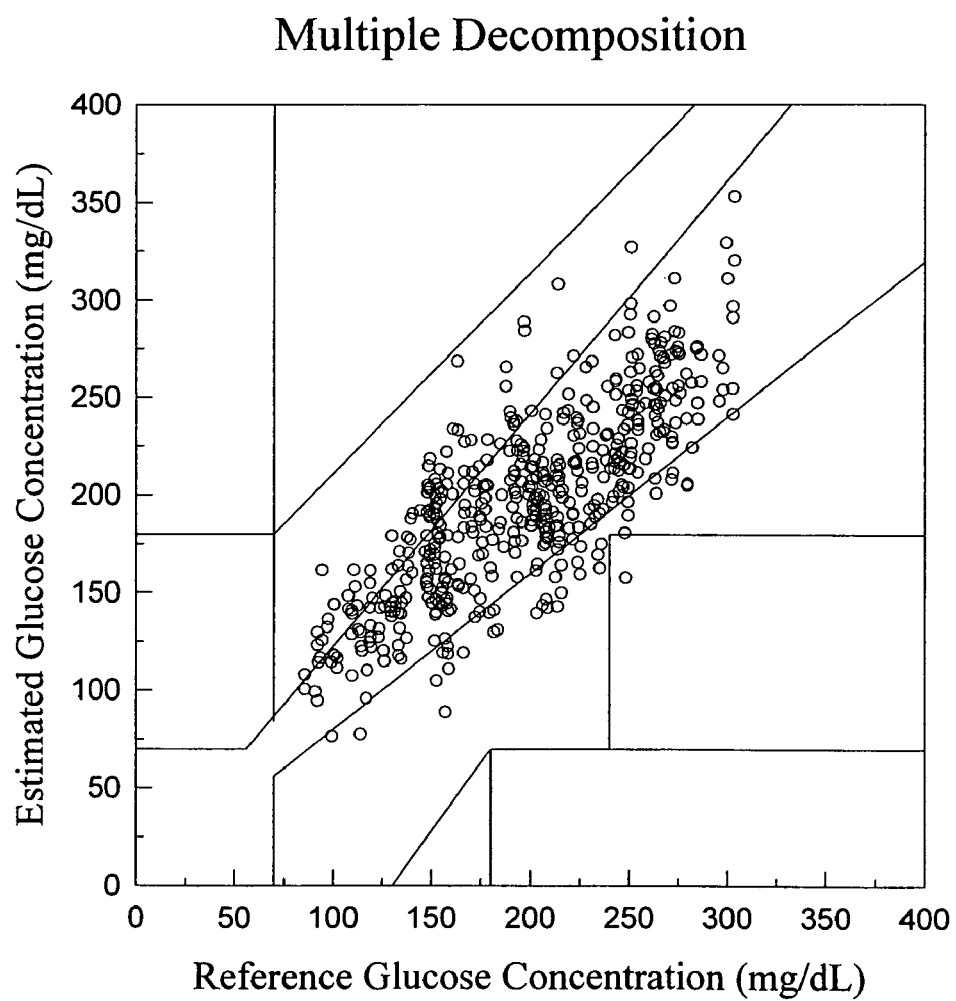
FIG. 9 provides a second example of noninvasive glucose concentration estimations in a concentration correlation plot according to the invention.

The dual region decomposition approach uses a first matrix associated with the spectral range of 1200 to 1400 nm and a second matrix associated with the spectral range of 1250 to 1780 nm. The first region is preprocessed in three steps: 1) a 21-point first derivative Savitsky-Golay smoothing convolution; 2) mean centering; and 3) selection of a data matrix associated with the 1200 to 1375 nm spectral range. The resulting matrix is decomposed and three factors are selected. The second region is preprocessed in three steps: 1) a 23-point first derivative Savitsky-Golay smoothing convolution; 2) mean centering; and 3) selection of a data matrix associated with the 1375 to 1850 nm spectral range. The resulting matrix is decomposed and 29 factors are selected. The scores matrices are then normalized, combined, and multiple linear regression is used to form a model. Use of the model, on the same data as used in the traditional approach above, results in a standard error of estimation of 20.1 mg/dL. The resulting glucose concentration estimations are presented in FIG. 9, which is overlaid onto a Clarke error grid. A total of 79.4, 20.6, and 0.0% of the glucose concentration estimations are in the A, B, and D regions of the Clarke error grid, respectively. Compared to the single decomposition approach, the dual decomposition approach results in a reduced standard error of estimation and an increased percentage of points in the 'A' region of a Clarke error grid. The resulting F-value is 4.7.

The separate decomposition of the individual matrices allows removal of the region of large variance from the first matrix associated with the 1200 to 1400 nm spectral range. This allows the initial factors in this region to capture major sources of variation represented by this region, such as scattering information and pathlength. The separate deconvolution of the overlapped 1375 to 1850 nm spectral range and the selection of more factors allows modeling of smaller variations, such as those due to fat, protein, and glucose. Combined, as demonstrated in this example, the separate decomposition of the individual matrices results in a reduction of the SEP from 42.1 to 20.1 mg/dL and results in an improved distribution of results in terms of the Clarke error grid analysis.

The above examples emphasize matrices representing data collected with near-infrared spectroscopy based techniques using biological samples. The invention is also useful for the analysis of matrices collected with other spectral regions, such as the ultraviolet, visible, and infrared, as well as with other techniques such as Raman and fluorescence. In addition, the invention is useful for the analysis of matrices of data collected using chromatographic based techniques, such as gas chromatography (GC), liquid chromatography (LC), super critical fluid chromatography (SCF), and capillary zone electrophoresis (CZE). Chromatographic techniques result in data matrices that have varying signal, noise, resolution, and interferences as a function of an axis, such as time. Extraction of an analyte property, such as a concentration, composition, or identity, from a matrix of data collected using chromatography with the invention is analogous to the extraction of properties from a matrix of data generated using spectroscopy. In addition, the invention is useful for analysis of data matrices representative of samples beyond biomedical, such as agricultural, pharmaceutical, and industrial.

The invention is applicable to applications involving imaging, especially when the signal, noise, and/or interference are non-uniform along an axis of the analyzed data matrix. In this application, each sample provides an N-dimensional matrix corresponding to an axis of the matrix, such as time, wavelength, frequency, or a spatial dimension. Data sub-blocks are selected from each of the N-dimensions and the sub-blocks are subjected to multi-dimensional preprocessing and decomposition.

Figure 10:
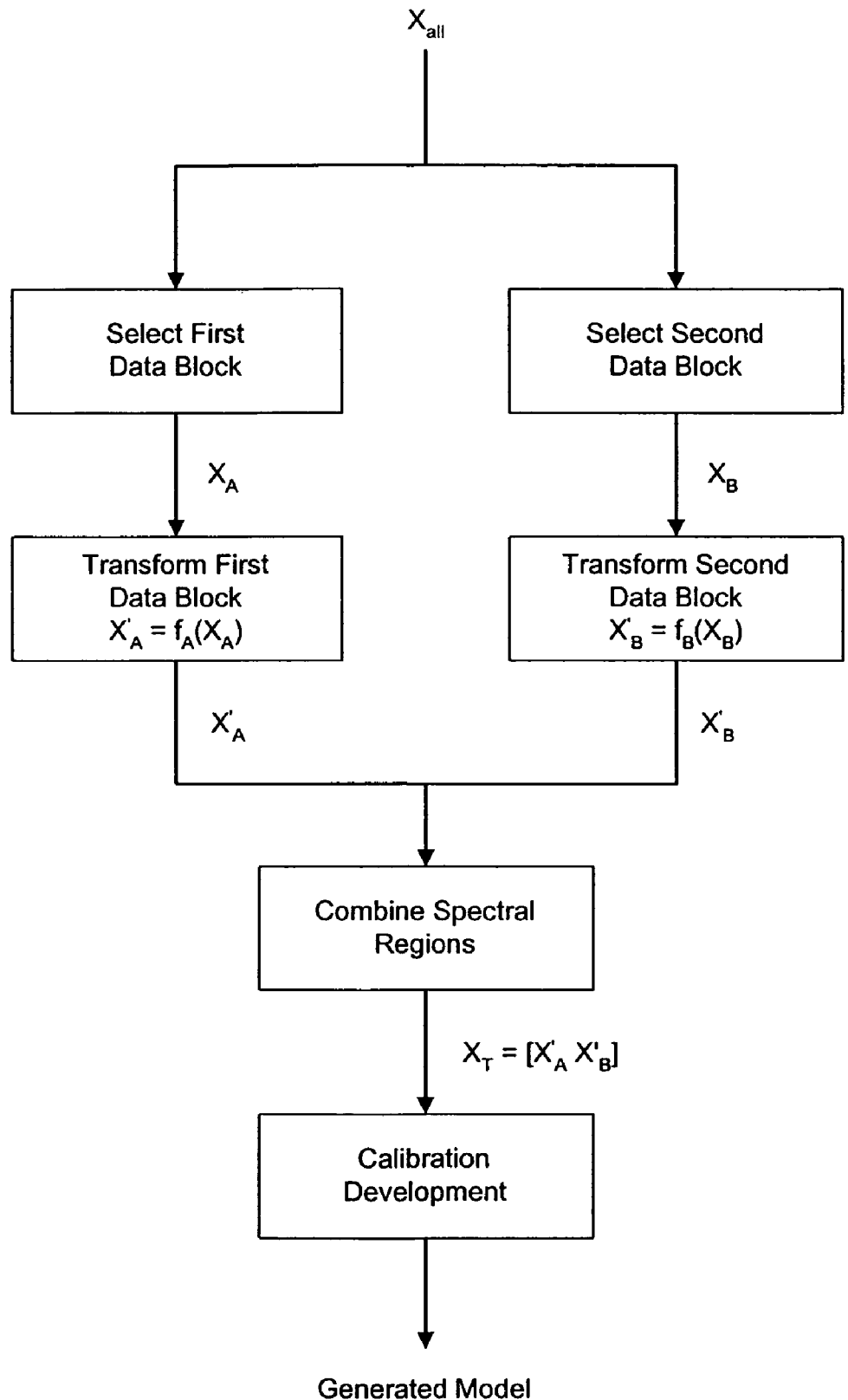
FIG. 10 provides a generalized two data block transformation according to the invention.

In its broadest sense, the invention is a transformation performed on N data blocks (where N is an integer≧2) generated from the initial data block $X_{all}$. Referring now to FIG. 10, an example is presented schematically using two data blocks associated with individual axis, such as an axis representing time, wavelength, or position. Two data blocks $X_A$ and $X_B$ are generated from $X_{all}$. The data blocks $X_A$ and $X_B$ are transformed according to equations 2 and 3, respectively.

$$X'_A = f_A(X_A) \quad (2)$$

$$X'_B = f_B(X_B) \quad (3)$$

The transformed data blocks are combined into a matrix $X_T$ according to equation 4.

$$X_T = [X'_A X'_B] \quad (4)$$

A calibration model is then developed from the combined spectral regions and is used for subsequent analysis.

Figure 11:
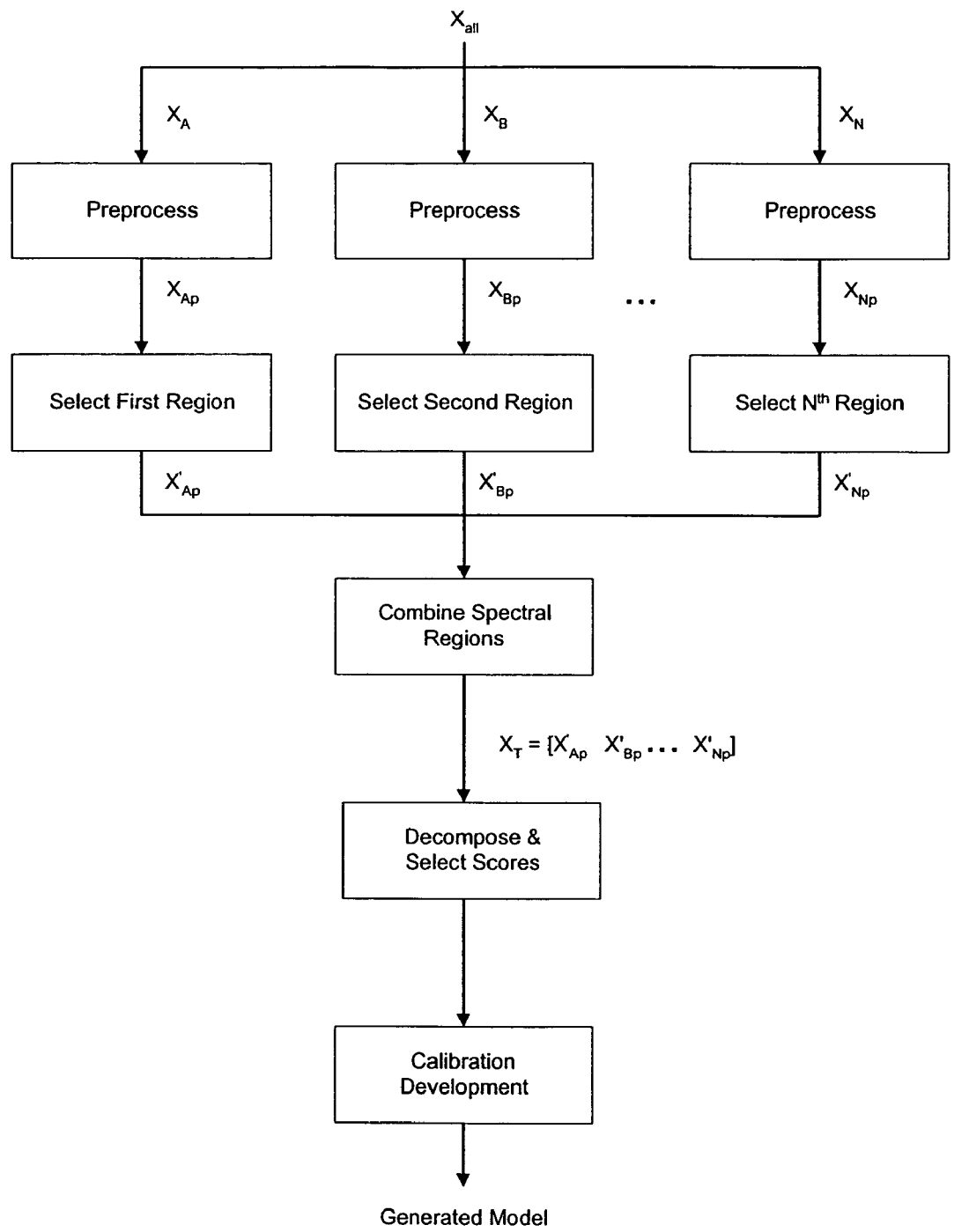
FIG. 11 provides a multiple region preprocessing approach to signal optimization according to the invention.

An alternative embodiment of the invention preprocesses multiple regions separately and combines the separately preprocessed regions into a single matrix for subsequent calibration. Referring now to FIG. 11, a series of data blocks $X_A, X_B, \ldots, X_N$ (where N is an integer≧2) are separately generated from an initial data block $X_{all}$. Each of the data blocks $X_A, X_B, \ldots, X_N$ are individually preprocessed to form data blocks $X_{Ap}, X_{Bp}, \ldots, X_{Np}$. Regions associated with data blocks $X_{Ap}, X_{Bp}, \ldots, X_{Np}$ are selected to form data blocks $X'_{Ap}, X'_{Bp}, \ldots, X'_{Np}$. Alternatively, the regions are selected from the blocks $X_A, X_B, \ldots, X_N$ and are subsequently individually preprocessed. The preprocessed and region selected data blocks are then concatenated according to equation 5, where $X_T$ is the combined data block.

$$X_T = [X'_{Ap} X'_{Bp} \ldots X'_{Np}] \quad (5)$$

The combined data block $X_T$ is subsequently decomposed and calibration development is performed to generate a model.

The invention finds particular utility in various spectroscopy applications, for example predicting concentration of analytes such as glucose from noninvasive near-IR spectra performed on live subjects. While the invention has been described herein with respect to near-IR spectroscopy, the invention is equally applicable to data matrices of any kind. In the chemical arts, spectroscopic techniques may include UV/VIS/NIR/IR, as well as techniques such as fluorescence, atomic absorption spectroscopy, nuclear magnetic resonance spectroscopy, and mass spectroscopy (MS). Furthermore, the invention is not limited to spectroscopic techniques but may include chromatographic techniques, such as GC/LC or combinations of chromatographic and spectroscopic techniques such as GC/MS or GC/IR. Additionally, the invention finds application in almost any field that relies on multivariate analysis techniques, such as the social sciences.

The presently preferred embodiment of the invention uses a sampling module coupled to a base module. The sampling module includes an illumination system based upon an incandescent lamp. The base module includes a grating and detector array. The base module may be connected to the sampling module through a communication bundle. In this document, the combined sampling module, communication bundle, base module, and associated electronics and software is referred to as a spectrometer. As in the preferred embodiment, a primary alternative embodiment of the invention includes two main modules: a sampling module and base module connected though a communication bundle. A number of spectrometer configurations are possible for this measurement as are outlined above. Basically the spectroscopic measurement system includes a source of near-infrared radiation, a wavelength selection system, an interface to the patient, photon guiding optics, and a detector. In one embodiment, the apparatus for noninvasive measurement of glucose through near-infrared spectroscopy, comprises: a base module comprising a grating and a detector array; a sampling module, securely and removeably attached to a sample site, and coupled to said base module, said sampling module comprising an illumination source; and a communication bundle for carrying optical and/or electrical signals between said base module and said sampling module, and for carrying power to said sampling module from said base module and optionally further comprises an optic system located before and/or after said sample site for coupling said illumination source to said sample and said sample to said detector array. The optic system optionally comprises an optical filter, a light blocker, and a standardization material. the apparatus further optionally comprises a communication bundle integrated between said sampling module and said base module.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

The invention claimed is:

1. A method for developing a calibration score matrix, comprising the steps of:
   providing a matrix of calibration spectra;
   generating N spectral matrices corresponding with N spectral regions of said calibration spectra, wherein N is an integer greater than or equal to two and wherein at least two of said N spectral regions are non-identical spectral regions;
   independently decomposing each of said N spectral matrices to yield N score matrices;
   independently selecting a plurality of factors for each of said N score matrices;
   concatenating said selected number of factors for each of said N score matrices, to generate a calibration score matrix, and
   estimating, with a spectrometer, a target property from a prediction matrix using said calibration score matrix, wherein said spectrometer comprises a base module, a communication bundle, and a sample module, wherein said communication bundle integrates said sampling module and said base module.

2. The method of claim 1, wherein N consists of any of the integers 2, 3, 4, and 5.

3. The method of claim 1, wherein said step of independently decomposing employs multivariate techniques.

4. The method of claim 3, wherein said multivariate techniques comprise any of:
   principal component analysis;
   partial least squares;
   wavelet regression;
   Fourier series;
   Taylor series; and
   factor analysis.

5. The method of claim 1, wherein at least two of said N spectral regions overlap.

6. The method of claim 1, wherein at least two of said N spectral regions are discontinuous regions.

7. The method of claim 1, wherein at least two of said N spectral regions abut.

8. The method of claim 1, further comprising the step of developing a calibration with said calibration score matrix.

9. The method of claim 8, further comprising the step of estimating said target property from an estimation spectrum.

10. The method of claim 1, further comprising the step of independently preprocessing each of said generated N spectral matrices prior to said step of decomposing.

11. The method of claim 10, further comprising the step of developing a calibration with said calibration score matrix.

12. The method of claim 11, wherein said calibration spectra comprise noninvasively obtained near-infrared spectra.

13. The method of claim 12, wherein at least two of said N spectral regions comprise regions within the first and second overtone spectral region.

14. The method of claim 13, further comprising the step of estimating a glucose concentration from a noninvasive spectrum.

15. A method for estimating a property from a noninvasive spectrum, comprising the steps of:
   providing a matrix of calibration spectra;
   generating N spectral matrices corresponding to N spectral regions of said calibration spectra, wherein N is an integer greater than or equal to two and wherein at least two of said N spectral regions are non-identical spectral regions;
   independently decomposing each of said N spectral matrices yielding N score matrices;
   independently selecting a plurality of factors to represent each of said N score matrices;
   concatenating said selected number of factors for each of said N score matrices to generate a calibration score matrix;
   generating a calibration model using said calibration score matrix; and
   estimating, with a spectrometer, a target property represented by said noninvasive spectrum, wherein said spectrometer comprises a base module, a communication bundle, and a sample module, wherein said communication bundle integrates said sampling module and said base module.

16. A method for developing a calibration for estimating a target property, comprising the steps of:
   providing a first calibration data block;
   generating N data blocks from said calibration data block, wherein N is an integer greater than or equal to two;
   transforming each of said N selected data blocks;
   combining said N transformed data blocks to form a second calibration matrix; and
   developing a calibration with said second calibration matrix; and
   estimating, with a spectrometer, a target property using said calibration, wherein said spectrometer comprises a base module, a communication bundle, and a sample module, wherein said communication bundle integrates said sampling module and said base module.

17. The method of claim 16, wherein said step of transforming comprises at least one of:
   independently preprocessing each of said N data blocks; and
   independently decomposing and selecting scores for each of said N data blocks.

18. The method of claim 1, wherein said target property comprises at least one of:
   an analyte concentration;
   an analyte composition; and
   an analyte constituent identification.

* * * * *